(12) United States Patent
Tsubuku et al.

(10) Patent No.: US 9,453,126 B2
(45) Date of Patent: Sep. 27, 2016

(54) CYANATE ESTER COMPOUND, CURABLE RESIN COMPOSITION CONTAINING CYANATE ESTER COMPOUND, AND CURED PRODUCT THEREOF

(75) Inventors: Makoto Tsubuku, Niigata (JP); Taketo Ikeno, Niigata (JP); Masayuki Katagiri, Niigata (JP); Tomoo Tsujimoto, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 93 days.

(21) Appl. No.: 13/878,584

(22) PCT Filed: Oct. 25, 2011

(86) PCT No.: PCT/JP2011/074559
§ 371 (c)(1),
(2), (4) Date: Jun. 25, 2013

(87) PCT Pub. No.: WO2012/057144
PCT Pub. Date: May 3, 2012

(65) Prior Publication Data
US 2013/0281640 A1 Oct. 24, 2013

(30) Foreign Application Priority Data
Oct. 29, 2010 (JP) .................. 2010-244696

(51) Int. Cl.
| | |
|---|---|
| *C08L 63/00* | (2006.01) |
| *C07C 261/02* | (2006.01) |
| *C08G 59/40* | (2006.01) |
| *C08G 73/06* | (2006.01) |
| *C08K 5/3415* | (2006.01) |
| *C09J 163/00* | (2006.01) |
| *C08L 79/08* | (2006.01) |

(52) U.S. Cl.
CPC .......... *C08L 63/00* (2013.01); *C07C 261/02* (2013.01); *C08G 59/4014* (2013.01); *C08G 73/0655* (2013.01); *C08K 5/3415* (2013.01); *C09J 163/00* (2013.01); *C07C 2101/14* (2013.01); *C08L 79/085* (2013.01)

(58) Field of Classification Search
CPC ................................................ C08G 73/0655
See application file for complete search history.

(56) References Cited

U.S. PATENT DOCUMENTS

| | | | |
|---|---|---|---|
| 3,553,244 A | 1/1971 | Grigat | |
| 4,839,442 A | 6/1989 | Craig | |
| 5,756,592 A | 5/1998 | Bedwell | |
| 6,121,484 A | 9/2000 | Falchetto | |
| 6,225,492 B1 | 5/2001 | Okamoto | |
| 2008/0200636 A1 | 8/2008 | Nakanishi et al. | |
| 2009/0130488 A1* | 5/2009 | Sugano et al. | 428/704 |
| 2009/0170983 A1* | 7/2009 | Tada et al. | 524/95 |
| 2012/0018072 A1 | 1/2012 | Ueno | |

FOREIGN PATENT DOCUMENTS

| | | |
|---|---|---|
| CN | 101283022 | 10/2008 |
| JP | 07-053497 | 2/1995 |
| JP | 07-070315 | 3/1995 |
| JP | 09-272737 | 10/1997 |
| JP | 2753831 | 6/1998 |
| JP | 2991054 | 10/1999 |
| JP | 2000-501138 | 2/2000 |
| JP | 2000-119239 | 4/2000 |
| JP | 2001-504835 | 4/2001 |
| JP | 2001-163972 | 6/2001 |
| JP | 2002-241469 | 8/2002 |
| JP | 2003-160639 | 6/2003 |
| JP | 2004-182816 | 7/2004 |
| JP | 2006-169317 | 6/2006 |
| JP | 2007-005750 | 1/2007 |
| JP | 2007-277102 | 10/2007 |
| JP | 2009-096874 | 5/2009 |
| JP | 2010-254838 | 11/2010 |
| JP | 2011-132167 | 7/2011 |
| TW | 1387608 | 3/2013 |

(Continued)

OTHER PUBLICATIONS

Ian Hamerton, "Chemistry and Technology of Cyanate Ester Resins", Blackie Academic & Professional, 1994, 1st edition, pp. 7-13, 54, 55.

(Continued)

*Primary Examiner* — Gregory Listvoyb
(74) *Attorney, Agent, or Firm* — Greenblum & Bernstein, P.L.C.

(57) ABSTRACT

There is provided a novel dicyanatophenyl-based difunctional cyanate ester which is in a liquid form at ordinary temperature and can obtain a cured product having an excellent low thermal expansion rate. There is disclosed a cyanate ester compound represented by the following formula (I):

[Formula 1]

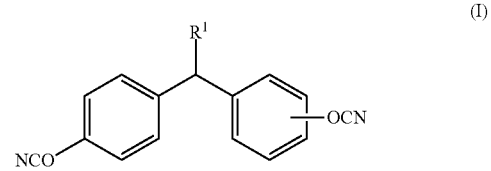

(I)

(wherein $R^1$ represents a hydrocarbon group having 2 to 20 carbon atoms).

17 Claims, 5 Drawing Sheets

(56) References Cited

FOREIGN PATENT DOCUMENTS

| | | |
|---|---|---|
| WO | 2007/049422 | 5/2007 |
| WO | 2010/109861 | 9/2010 |

OTHER PUBLICATIONS

International Search Report issued in connection with counterpart PCT/JP2011/074559 on Jan. 24, 2012.

* cited by examiner

CYANATE ESTER COMPOUND, CURABLE RESIN COMPOSITION CONTAINING CYANATE ESTER COMPOUND, AND CURED PRODUCT THEREOF

BACKGROUND OF THE INVENTION

1. Technical Field

The present invention relates to a novel cyanate ester compound, a curable resin composition containing the novel cyanate ester compound, and a cured product thereof. More particularly, the present invention relates to a novel cyanate ester compound used for a resin composition being in a liquid form at ordinary temperature and capable of improving a thermal expansion rate of a cured product.

2. Background Art

In recent years, there have been many electronic devices having light, thin, short and compact as keywords, such as a mobile phone, an ultraslim liquid crystal TV and plasma TV, and a lightweight laptop in the field of a semiconductor-related material. Therefore, very high performance has been required for a package material. Particularly, a tip package has a complicated structure, which in turn increases the number of elements that cannot easily be sealed by sealing other than liquid sealing. For example, it is necessary to partially seal an element having a cavity-down-type structure such as EBGA but transfer molding cannot handle the element. For such a reason, development of a highly-functional liquid curable resin material as a sealing material has been required.

In case of the liquid sealant, because of the difficulty of highly filling of a filler and raising of Tg (glass transition temperature) of a matrix resin itself unlike a powder sealing material, the coefficient of thermal expansion of the sealing material tends to be increased. Therefore, the liquid sealing material has solder heat resistance and heat shock resistance inferior to those of the powder sealing material subjected to transfer molding. As a result, a crack in a resin or a chip is more likely to be generated by a stress generated by the difference between the coefficient of thermal expansion of the liquid sealing material and the coefficient of thermal expansion of a chip, which disadvantageously reduces the reliability of a semiconductor device. Therefore, a resin for a liquid sealing material, which has high Tg and a low coefficient of thermal expansion, has been required.

Epoxy resin compositions containing a bisphenol A-based epoxy resin or an alicyclic epoxy resin or the like as a main component, a liquid acid anhydride or phenol novolac as a curing agent, and an additive such as an inorganic filler are proposed as liquid sealing resin compositions for sealing a semiconductor element (for example, see Patent Documents 1, 2, and 3). However, the resin composition containing the bisphenol A-based epoxy resin or the alicyclic epoxy resin or the like as the main component has low Tg and a larger coefficient of thermal expansion in a high temperature range. These resin compositions also have a large dielectric constant and dielectric loss in a high-frequency region, which do not necessarily satisfy the requirements of miniaturization, high density, and speeding up of the semiconductor device.

On the other hand, a cyanate ester resin has been known through the ages as a thermosetting resin having excellent heat resistance as well as a low dielectric constant and low dielectric loss. Particularly, a resin composition using a bisphenol A-based cyanate ester resin and a bismaleimide compound in combination, as proposed in Patent Document 4, is referred to as a BT resin. Since the BT resin has excellent electrical characteristics, mechanical characteristics, and chemical resistance or the like, the BT resin is suitable for a sealing material of the semiconductor element. However, because the bisphenol A-based cyanate ester is a crystalline compound having a melting point of 80° C., the bisphenol A-based cyanate ester cannot be used as it is as a liquid sealing material, and it is necessary to use the bisphenol A-based cyanate ester and other component being in a liquid form at ordinary temperature in combination. However, the combined use of other component is influenced by the added component and reduces the degree of freedom of blending of the composition, which may hinder functional improvement.

For example, Patent Document 5 discloses a resin composition containing a cyanate ester compound using a triphenylmethane-based cyanate ester compound to improve thermal expansibility. However, the triphenylmethane-based cyanate ester compound is a solid at ordinary temperature, and is insufficient for the liquid sealing material. Furthermore, Patent Document 6 discloses that a difunctional cyanatophenyl-based cyanate ester compound in which two cyanatophenyl groups are bonded via an asymmetric alkylene group has a low viscosity and non-crystallinity, and a resin cured product using the compound has an excellent heat deflection temperature and flexural strength. Patent Document 6 discloses bis(4-cyanatophenyl)-2,2-propane, bis(4-cyanatophenyl)-1,1-ethane, and bis(4-cyanatophenyl)-2,2-butane or the like as examples thereof.

CITATION LIST

Patent Document

Patent Document 1 Japanese Patent Laid-Open No. 2002-241469
Patent Document 2 Japanese Patent Laid-Open No. 2003-160639
Patent Document 3 Japanese Patent Laid-Open No. 2007-5750
Patent Document 4 Japanese Patent Laid-Open No. H7-70315
Patent Document 5 Japanese Patent Laid-Open No. 2006-169317
Patent Document 6 Japanese Patent Publication No. 2753831

SUMMARY OF INVENTION

The present inventors have found that a specific difunctional cyanate ester compound as a cyanate ester resin, above all, a difunctional cyanate ester compound obtained by substituting hydrogen of a methylene group bonded to cyanatophenyl groups with a specific alkyl group is in a liquid form at ordinary temperature and can realize a cured product having an excellent low thermal expansion rate and heat resistance. The present invention was accomplished based on this finding.

Therefore, it is an object of the present invention to provide a novel difunctional cyanatophenyl-based cyanate ester which is in a liquid form at ordinary temperature and can obtain a cured product having an excellent low thermal expansion rate.

It is another object of the present invention to provide a curable resin composition containing the cyanate ester compound.

The cyanate ester compound according to the present invention is represented by the following formula (I):

[Formula 1]

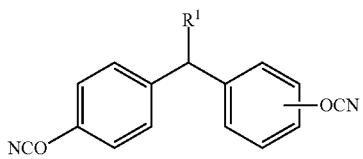

(I)

(wherein R¹ represents a hydrocarbon group having 2 to 20 carbon atoms).

In an embodiment of the present invention, the compound of the formula (I) is preferably 1,1-bis(4-cyanatophenyl) isobutane.

A curable resin composition according to another aspect of the present invention contains the cyanate ester compound represented by the above formula (I).

Furthermore, another aspect of the present invention also provides a cured product obtained by curing the above curable resin composition, and a sealing material and an adhesive containing the above curable resin composition.

The curable resin composition containing the cyanate ester compound represented by the above formula (I) is in a liquid form at ordinary temperature and can realize the cured product having an excellent low coefficient of thermal expansion and heat resistance according to the present invention.

SPECIFIC DESCRIPTION OF THE INVENTION

<Cyanate Ester Compound>

Figure 1:
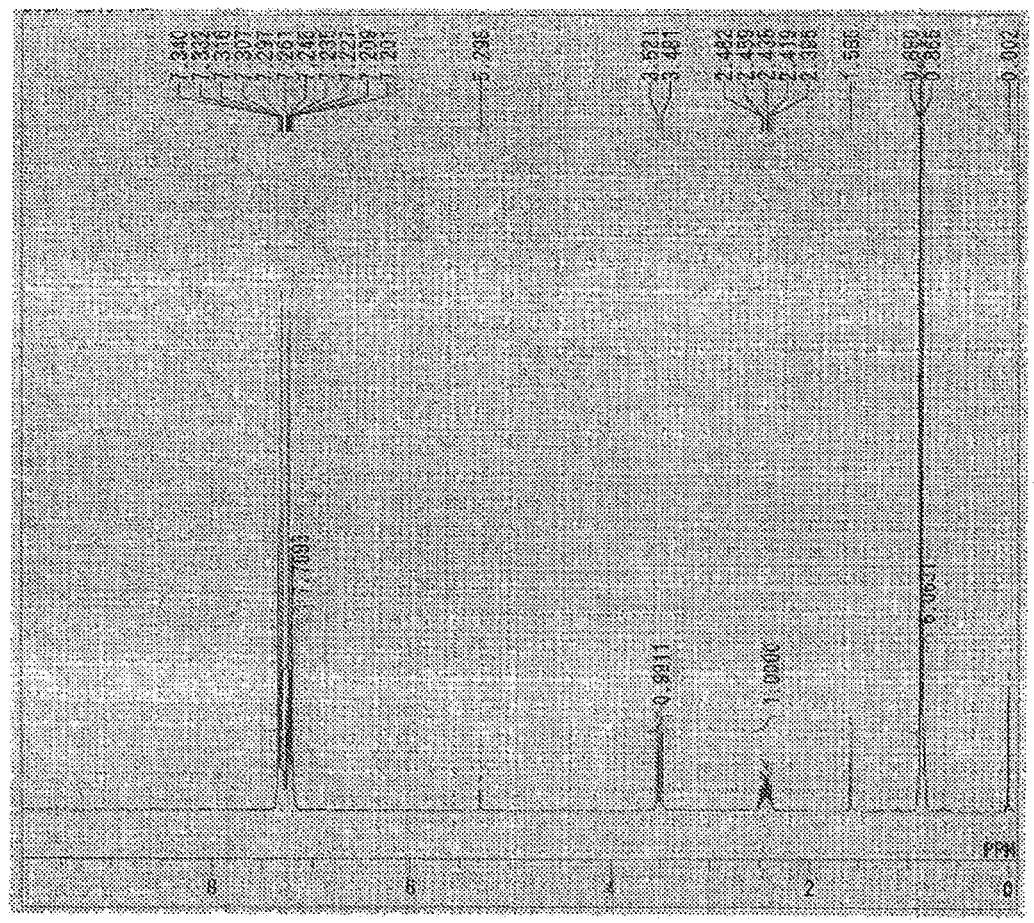
FIG. 1 shows a ¹H-NMR chart of 1,1-bis(4-cyanatophenyl)isobutane obtained in Synthesis Example 1.

A cyanate ester compound according to the present invention is represented by the following formula (I):

[Formula 2]

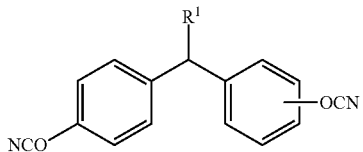

(I)

(wherein R¹ represents a hydrocarbon group having 2 to 20 carbon atoms). Examples of the cyanate ester include 1,1-bis(4-cyanatophenyl)propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 1,1-bis(4-cyanatophenyl)hexane, 1,1-bis(4-cyanatophenyl)-4-methylpentane, 1,1-bis(4-cyanatophenyl)-3-methylpentane, 1,1-bis(4-cyanatophenyl)-2-methylpentane, 1,1-bis(4-cyanatophenyl)-2,3-dimethylbutane, 1,1-bis(4-cyanatophenyl)-3,3-dimethylbutane, bis(4-cyanatophenyl)cyclopentylmethane, bis(4-cyanatophenyl)cyclohexyl methane, bis(4-cyanatophenyl) phenylmethane, 1,1-bis(4-cyanatophenyl)heptane, 1,1-bis(4-cyanatophenyl)-2-methylhexane, 1,1-bis(4-cyanatophenyl)-3-methylhexane, 1,1-bis(4-cyanatophenyl)-4-methylhexane, 1,1-bis(4-cyanatophenyl)-5-methylhexane, 1,1-bis(4-cyanatophenyl)-3,4-dimethylpentane, 1,1-bis(4-cyanatophenyl)-2,3-dimethylpentane, 1,1-bis(4-cyanatophenyl)-3-ethylpentane, 1,1-bis(4-cyanatophenyl)-2-ethylpentane, bis(4-cyanatophenyl)-1-naphthylmethane, 1,1-bis(4-cyanatophenyl)-2-phenylmethylhexane, 1-(2-cyanatophenyl)-1-(4-cyanatophenyl)propane, 1-(2-cyanatophenyl)-1-(4-cyanatophenyl)butane, 1-(2-cyanatophenyl)-1-(4-cyanatophenyl)isobutane, 1-(2-cyanatophenyl)-1-(4-cyanatophenyl)pentane, 1-(2-cyanatophenyl)-1-(4-cyanatophenyl)-3-methylbutane, 1-(2-cyanatophenyl)-1-(4-cyanatophenyl)-2-methylbutane, 1-(2-cyanatophenyl)-1-(4-cyanatophenyl)-2,2-dimethylpropane, 1-(2-cyanatophenyl)-1-(4-cyanatophenyl)hexane, 1-(2-cyanatophenyl)-1-(4-cyanatophenyl)-4-methylpentane, 1-(2-cyanatophenyl)-1-(4-cyanatophenyl)-3-methylpentane, 1-(2-cyanatophenyl)-1-(4-cyanatophenyl)-2-methylpentane, 1-(2-cyanatophenyl)-1-(4-cyanatophenyl)-2,3-dimethylbutane, 1-(2-cyanatophenyl)-1-(4-cyanatophenyl)-3,3-dimethylbutane, [(2-cyanatophenyl)-(4-cyanatophenyl)methyl]cyclopentane, [(2-cyanatophenyl)-(4-cyanatophenyl)methyl] cyclohexane, 2,4'-dicyanatotriphenylmethane, 1-(2-cyanatophenyl)-1-(4-cyanatophenyl)heptane, 1-(2-cyanatophenyl)-1-(4-cyanatophenyl)-2-methylhexane, 1-(2-cyanatophenyl)-1-(4-cyanatophenyl)-3-methylhexane, 1-(2-cyanatophenyl)-1-(4-cyanatophenyl)-4-methylhexane, 1-(2-cyanatophenyl)-1-(4-cyanatophenyl)-5-methylhexane, 1-(2-cyanatophenyl)-1-(4-cyanatophenyl)-3,4-dimethylpentane, 1-(2-cyanatophenyl)-1-(4-cyanatophenyl)-2,3-dimethylpentane, 1-(2-cyanatophenyl)-1-(4-cyanatophenyl)-3-ethylpentane, 1-(2-cyanatophenyl)-1-(4-cyanatophenyl)-2-ethylpentane, and [(2-cyanatophenyl)-(4-cyanatophenyl)methyl] naphthalene.

Of the above cyanate esters, 1,1-bis(4-cyanatophenyl) propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 1,1-bis(4-cyanatophenyl)-2,3-dimethylbutane, 1,1-bis(4-cyanatophenyl)-3,3-dimethylbutane, cyclopentyl bis(4-cyanatophenyl)methane, cyclohexyl bis(4-cyanatophenyl)methane, and bis(4-cyanatophenyl)phenylmethane are preferable, and particularly, 1,1-bis(4-cyanatophenyl)propane, 1,1-bis(4-cyanatophenyl)butane, 1,1-bis(4-cyanatophenyl)isobutane, 1,1-bis(4-cyanatophenyl) pentane, 1,1-bis(4-cyanatophenyl)-3-methylbutane, 1,1-bis (4-cyanatophenyl)-2-methylbutane, 1,1-bis(4-cyanatophenyl)-2,2-dimethylpropane, 1,1-bis(4-cyanatophenyl)-2,3-dimethylbutane, 1,1-bis(4-cyanatophenyl)-3,3-dimethylbutane, and cyclopentyl bis(4-cyanatophenyl)methane are more preferable, and further, 1,1-bis(4-cyanatophenyl)propane, 1,1-bis(4-cyanatophenyl) isobutane, and 1,1-bis(4-cyanatophenyl)-2,2-dimethylpropane are even more preferable. Above all, because 1,1-bis (4-cyanatophenyl)isobutene having a structure obtained by substituting one of hydrogens in a methylene group (—CH₂—) bonded to the cyanatophenyl groups with an isopropyl group is in a liquid form at ordinary temperature, 1,1-bis(4-cyanatophenyl)isobutene is suitable for a resin for a liquid sealing material. 1,1-Bis(4-cyanatophenyl)isobutene is a non-crystalline liquid, and has little change in physical properties under a high temperature atmosphere. Furthermore, the coefficient of linear expansion of a cured product of the curable resin composition containing 1,1-bis(4-cyanatophenyl)isobutane as the cyanate ester compound is smaller under high temperature than that of a resin composition containing a dicyanatophenyl-based difunctional cyanate ester obtained by substituting the hydrogen in the methylene group (—CH$_2$—) with the other alkyl group, and therefore, a resin composition for a liquid sealing material having excellent heat resistance can be realized. It is, of course, needless to say that even when the curable resin composition contains 1,1-bis(4-cyanatophenyl)isobutene as the cyanate ester compound, the curable resin composition may further contain the above other difunctional cyanate ester compound in addition to that.

A method for producing the cyanate ester compound represented by the above formula (I) is not particularly limited. A desired compound can be obtained by applying a method known as a cyanate synthetic method using a phenol represented by the following formula (V).

[Formula 3]

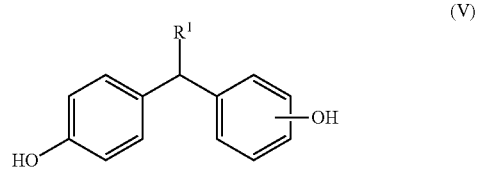

(V)

(wherein R$^1$ is the same as the definition of the above formula (I)).

For example, the cyanate ester compound of the above formula (I) can be obtained by cyanation of the phenol of the above formula (V) according to a method described in IAN HAMERTON, "Chemistry and Technology of Cyanate Ester Resins", BLACKIE ACADEMIC & PROFESSIONAL. The following methods are also known: a method for reacting a cyanogen halide in the presence of a base in a solvent under such a condition that the cyanogen halide always exists excessively over the base (U.S. Pat. No. 3,553,244); a synthetic method for using a tertiary amine as a base and using it excessively over cyanogen halide (Japanese Patent Laid-Open No. H7-53497); a method for reacting trialkylamine and cyanogen halide in a continuous plug flow system (National Publication of International Patent Application No. 2000-501138); a method for reacting a phenol and a cyanogen halide in the presence of a tert-amine in a non-aqueous solution while processing the by-product of tert-ammonium halide with an anion/cation exchange pair (National Publication of International Patent Application No. 2001-504835); a method for reacting a tertiary amine and cyanogen halide through simultaneous addition in the presence of a solvent capable of separating a phenol compound from water, then washing it with water and subjecting it to liquid-liquid separation, followed by precipitation and purification from the obtained solution by the use of a poor solvent such as a secondary or tertiary alcohol and hydrocarbon. (Japanese Patent Publication No. 2991054); and a method for causing naphthols, a cyanogen halide and a tertiary amine to react under an acidic condition in a two-phase solvent of water and an organic solvent (Japanese Patent Laid-Open No. 2007-277102). In the present invention, the cyanate ester compound can be obtained by suitably using these methods. The cyanate ester compound obtained by the above method can be identified by known methods such as NMR.

<Curable Resin Composition>

The curable resin composition according to the present invention contains the cyanate ester compound (A) represented by the above formula (I). In the present invention, the curable resin composition may contain other compounds in addition to the cyanate ester compound (A) represented by the above formula (I). The curable resin composition preferably contains at least one or more of a cyanate ester compound (B) represented by the following general formula (II) or (III), an epoxy resin (C), and a maleimide compound (D).

[Formula 4]

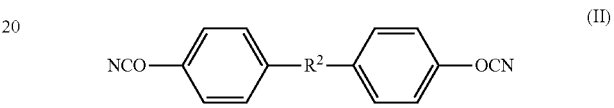

(II)

(wherein R$^2$ represents any one selected from the group consisting of the following general formulae (i) to (v):

[Formula 5]

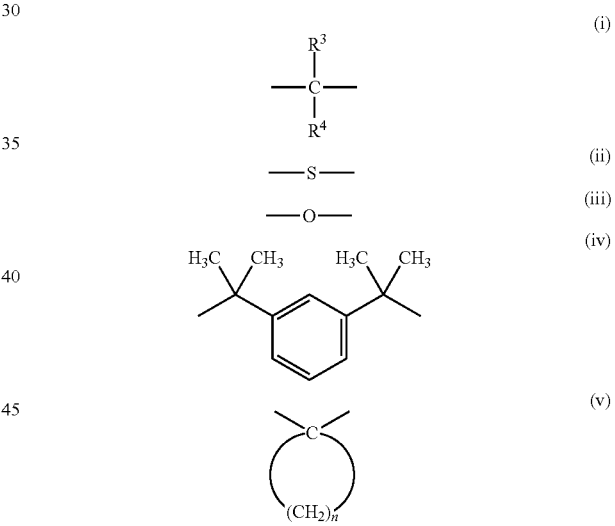

(i)
(ii)
(iii)
(iv)
(v)

[wherein each of R$^3$ and R$^4$ represents a hydrogen atom, or an alkyl group having 1 to 8 carbon atoms or a trifluoromethyl group, and n represents an integer of 4 to 7].

[Formula 6]

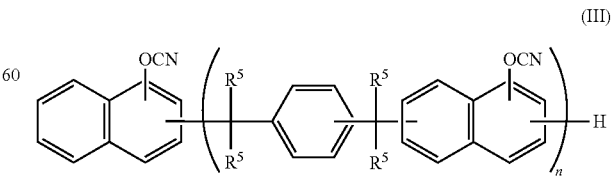

(III)

(wherein R$^5$ represents hydrogen or a methyl group; n represents an integer of 1 to 50; and the cyanate ester compound (B) represented by the general formula (III) may be a mixture of compounds having different n).

The cyanate ester compound represented by the above general formula (II) can be obtained by cyanation of a phenol represented by the following general formula (VI) according to the same method as that described above.

[Formula 7]

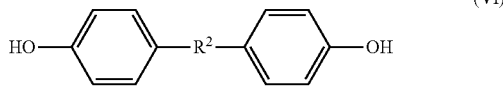

(VI)

(wherein $R^2$ is the same as the above definition).

The cyanate ester compound represented by the above general formula (III) can be obtained by cyanation of a phenol represented by the following general formula (VII) according to the same method as that described above.

[Formula 8]

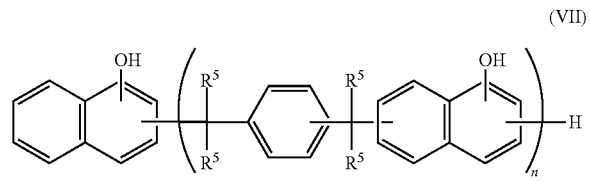

(VII)

(wherein $R^5$ and n are the same as the above definitions).

As the cyanate ester compound (B) represented by the above general formulae (II) and (III), which may be contained as an optional component in the curable resin composition, any commonly-known cyanate ester compound can be used. Examples thereof include bis(4-cyanatophenyl)methane, 2,4'-dicyanatodiphenylmethane, 1,1-bis(4-cyanatophenyl)ethane, 2,2-bis(4-cyanatophenyl)propane, 2,2-bis(4-cyanatophenyl)butane, 2,2-bis(4-cyanatophenyl)pentane, 2,2-bis(4-cyanatophenyl)hexane, 2,2-bis(4-cyanatophenyl)-3-methylbutane, 2,2-bis(4-cyanatophenyl)4-methylpentane, 2,2-bis(4-cyanatophenyl)-3-methylpentane, 2,2-bis(4-cyanatophenyl)-3,3-dimethylbutane, 3,3-bis(4-cyanatophenyl)hexane, 3,3-bis(4-cyanatophenyl)heptane, 3,3-bis(4-cyanatophenyl)octane, 3,3-bis(4-cyanatophenyl)-2-methylpentane, 3,3-bis(4-cyanatophenyl)-2-methylhexane, 3,3-bis(4-cyanatophenyl)-2,2-dimethylpentane, 4,4-bis(4-cyanatophenyl)-3-methylheptane, 3,3-bis(4-cyanatophenyl)-2-methylheptane, 3,3-bis(4-cyanatophenyl)-2,2-dimethylhexane, 3,3-bis(4-cyanatophenyl)-2,4-dimethylhexane, 3,3-bis(4-cyanatophenyl)-2,2,4-trimethylpentane, 2,2-bis(4'-cyanatophenyl)-1,1,1,3,3,3-hexafluoropropane, 1,3-bis[2-(4-cyanatophenyl)-2-propyl]benzene, bis-(4-cyanatophenyl)ether, bis-(4-cyanatophenyl)sulfide, 1,3-bis(4-cyanato-α,α-dimethylbenzyl)benzene, 1,1-bis(4'-cyanatophenyl)cyclopentane, and 1,1-bis(4'-cyanatophenyl)cyclohexane.

Among these, bis(4-cyanatophenyl)methane, 2,4'-dicyanatodiphenylmethane, 1,1-bis(4-cyanatophenyl)ethane, 2,2-bis(4-cyanatophenyl)butane, 2,2-bis(4-cyanatophenyl)hexane, 2,2-bis(4-cyanatophenyl)4-methylpentane, 2,2-bis(4-cyanatophenyl)-3,3-dimethylbutane, 3,3-bis(4-cyanatophenyl)hexane, 3,3-bis(4-cyanatophenyl)-2-methylpentane, 2,2-bis(4'-cyanatophenyl)-1,1,1,3,3,3-hexafluoropropane, 1,3-bis[2-(4-cyanatophenyl)-2-propyl]benzene, bis-(4-cyanatophenyl)ether, bis-(4-cyanatophenyl)sulfide, 1,1-bis(4'-cyanatophenyl)cyclopentane, and 1,1-bis(4'-cyanatophenyl)cyclohexane are preferable, and bis(4-cyanatophenyl)methane, 2,4'-dicyanatodiphenylmethane, 1,1-bis(4-cyanatophenyl)ethane, 2,2-bis(4-cyanatophenyl)propane, 2,2-bis(4-cyanatophenyl)butane, 2,2-bis(4-cyanatophenyl)4-methylpentane, 2,2-bis(4'-cyanatophenyl)-1,1,1,3,3,3-hexafluoropropane, 1,3-bis[2-(4-cyanatophenyl)-2-propyl]benzene, bis-(4-cyanatophenyl)ether, bis-(4-cyanatophenyl)sulfide, and 1,1-bis(4'-cyanatophenyl)cyclohexane are more preferable. These cyanate ester compounds can be used alone or in mixtures of two or more.

As the epoxy resin (C) contained as the optional component in the curable resin composition, any commonly-known epoxy resin can be used, as long as it has two or more epoxy groups in its molecule. Examples thereof include a bisphenol A-based epoxy resin, a bisphenol F-based epoxy resin, a phenol novolac-based epoxy resin, a cresol novolac-based epoxy resin, a bisphenol A novolac-based epoxy resin, a brominated bisphenol A-based epoxy resin, a brominated phenol novolac-based epoxy resin, a trifunctional phenol-based epoxy resin, a tetrafunctional phenol-based epoxy resin, a naphthalene-based epoxy resin, a biphenyl-based epoxy resin, a phenol aralkyl-based epoxy resin, a biphenyl aralkyl-based epoxy resin, a naphthol aralkyl-based epoxy resin, an alicyclic epoxy resin, a polyol-based epoxy resin, a phosphorus-containing epoxy resin, glycidyl amine, glycidyl ester, a compound obtained by epoxidizing double bond such as butadiene, and a compound obtained by reaction of hydroxyl group-containing silicone resins with epichlorohydrin. Among these, the bisphenol A-based epoxy resin, the bisphenol F-based epoxy resin, the phenol novolac-based epoxy resin, the cresol novolac-based epoxy resin, the brominated bisphenol A-based epoxy resin, the brominated phenol novolac-based epoxy resin, the naphthalene-based epoxy resin, the biphenyl-based epoxy resin, the phenol aralkyl-based epoxy resin, the biphenyl aralkyl-based epoxy resin, the naphthol aralkyl-based epoxy resin, the alicyclic epoxy resin, the polyol-based epoxy resin, the phosphorus-containing epoxy resin, glycidyl amine, and glycidyl ester or the like are preferable. The bisphenol A-based epoxy resin, the bisphenol F-based epoxy resin, the naphthalene-based epoxy resin, the biphenyl-based epoxy resin, the phenol aralkyl-based epoxy resin, the biphenyl aralkyl-based epoxy resin, the naphthol aralkyl-based epoxy resin, and the alicyclic epoxy resin or the like are more preferable. These epoxy resins can be used alone or in mixtures of two or more.

A compound represented by the following general formula (IV) can be suitably used as the maleimide compound (D) contained as the optional component in the curable resin composition:

[Formula 9]

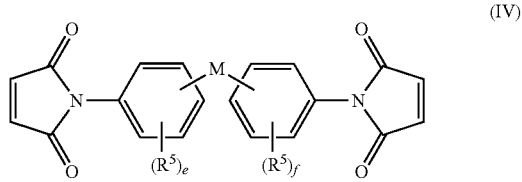

(IV)

(wherein each of $R^5$ and $R^6$ independently represents a hydrogen atom, a halogen atom, or an alkyl group having 1 to 3 carbon atoms; each of e and f each represents an integer of 1 to 4; and M represents a single bond, an alkylene group having 1 to 5 carbon atoms or an alkylidene group having 1 to 5 carbon atoms, or an arylene group having 6 to 14 carbon atoms).

As the maleimide compound represented by the above general formula (IV), bis(4-maleimidephenyl)methane, 2,2-bis[4-(4-maleimidephenoxy)phenyl]propane, bis(3,5-dimethyl-4-maleimidephenyl)methane, bis(3-ethyl-5-methyl-4-maleimidephenyl)methane, and bis(3,5-diethyl-4-maleimidephenyl)methane are preferable. Examples of the maleimide compound (D) include a prepolymer of the above maleimide compound or a prepolymer of a maleimide compound and an amine compound. These compounds and prepolymers can be used alone or in mixtures of two or more as needed.

In the present invention, the curable resin composition preferably contains 0 to 250 parts by mass of the cyanate ester compound (B), 0 to 250 parts by mass of the epoxy resin (C), and 0 to 100 parts by mass of the maleimide compound (D), based on 100 parts by mass of the cyanate ester compound (A). The curable resin composition more preferably contains 0 to 100 parts by mass of the cyanate ester compound (B), 0 to 100 parts by mass of the epoxy resin (C), and 0 to 50 parts by mass of the maleimide compound (D). The curable resin composition containing the compounds and the resins at the above ratios can lower the coefficient of linear expansion of the cured product under high temperature, and has excellent heat resistance.

In the present invention, in addition to the above compounds (A) to (D), a benzoxazine compound and/or a compound having a polymerizable unsaturated group, or the like can also be added. The benzoxazine compound may be any ordinary known one, as long as it has two or more dihydrobenzoxazine rings in its molecule. Examples thereof include a benzoxazine compound described in Japanese Patent Laid-Open No. 2009-096874. These benzoxazine compounds can be used alone or in mixtures of two or more.

The above compound having the polymerizable unsaturated group may be any ordinary known one. Examples thereof include vinyl compounds such as ethylene, propylene, styrene, divinylbenzene, and divinylbiphenyl; mono or polyalcohol(meth)acrylates such as methyl(meta)acrylate, 2-hydroxyethyl(meta)acrylate, 2-hydroxypropyl(meta)acrylate, polypropyleneglycol di(meta)acrylate, trimethylolpropane di(meta)acrylate, trimethylolpropane tri(meta)acrylate, pentaerythritol tetra(meta)acrylate, and dipentaerythritol hexa(meta)acrylate; epoxy(meth)acrylates such as bisphenol A-based epoxy(meth)acrylate and bisphenol F-based epoxy(meth)acrylate; and benzocyclobutene resins. These compounds having an unsaturated group can be used alone or in mixtures of two or more.

The curable resin composition according to the present invention may further contain a compound which catalyzes the polymerization of a cyanate ester; an epoxy resin; an oxetane resin; or the compound having a polymerizable unsaturated group, in addition to the above compounds and resins. Examples of the polymerization catalyst include metal complex compounds containing zinc such as zinc octylate, zinc stearate, zinc naphthenate, and zinc acetylacetone; phenol compounds such as octyl phenol and nonyl phenol; alcohols such as 1-butanol and 2-ethylhexanol; imidazole derivatives such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethyl imidazole, and 2-phenyl-4-methyl-5-hydroxymethyl imidazole; amine compounds such as dicyandiamide, benzyldimethylamine, 4-methyl-N,N-dimethylbenzylamine; and phosphine-based or a phosphonium-based phosphorus compounds. Epoxy-imidazole adduct-based compounds; peroxides such as benzoyl peroxide, p-chlorobenzoyl peroxide, di-t-butyl peroxide, diisopropyl peroxycarbonate, and di-2-ethylhexyl peroxycarbonate; or azo compounds such as azobisisobutyronitrile may be used. These catalysts may be commercial products. Examples thereof include Amicure PN-23 (manufactured by Ajinomoto Fine-Techno Co., Inc.), Novacure HX-3721 (manufactured by ASAHI CHEMICAL INDUSTRY CO., LTD.), and Fujicure FX-1000 (manufactured by the FUJI KASEI, Co., Ltd.).

Of the above polymerization catalysts, the metal complex compound containing zinc is particularly preferable. A cured product having more excellent heat resistance and a lower thermal expansion rate can be realized by using the metal complex compound and the cyanate ester compound represented by the above formula (I) in combination.

The curable resin composition according to the present invention may contain an inorganic filler. Examples of the inorganic filler include silicates such as talc, calcined clay, uncalcined clay, mica, and glass; oxides such as titanium oxide, alumina, silica, and fused silica; carbonates such as calcium carbonate, magnesium carbonate, and hydrotalcite; hydroxides such as aluminum hydroxide, magnesium hydroxide, and calcium hydroxide; sulfates or sulfites such as barium sulfate, calcium sulfate, and calcium sulfite; borates such as zinc borate, barium metaborate, aluminum borate, calcium borate, and sodium borate; nitrides such as aluminum nitride, boron nitride, silicon nitride, and carbon nitride; and titanates such as strontium titanate and barium titanate. One of these can be used alone or two or more thereof may be used in combination. Among these, silica is particularly preferable, and fused silica is preferable in respect of excellent low thermal expansibility. Although granular type and spherical silicas exist, the spherical silica is preferable in respect of lowering the melt viscosity of the resin composition.

The spherical silica may be further processed by a processing agent for previously performing a surface treatment. At least one or more compounds selected from the group consisting of functional group-containing silanes, annular oligosiloxanes, organohalosilanes, and alkylsilazanes may be suitably used as the processing agent. Among these, the spherical silica is suitably subjected to the surface treatment using the organohalosilanes and the alkylsilazanes in order to make the surface of the spherical silica hydrophobic. The surface treatment using the organohalosilanes and the alkylsilazanes is also preferable in respect of excellent dispersibility of the spherical silica in the curable resin composition.

The functional group-containing silanes used as the processing agent are not particularly limited. Examples thereof include epoxysilane compounds such as 3-glycidoxypropyltrimetoxysilane, 3-glycidoxypropyltriethoxysilane, 3-glycidoxypropylmethyldiethoxysilane, and 2-(3,4-epoxycyclohexyl)ethyldimethoxysilane; (meth)acrylsilanes such as 3-methacryloxypropyltrimethoxysilane, 3-methacryloxypropylmethyldimethoxysilane, 3-methacryloxypropyltriethoxysilane, and 3-methacryloxypropylmethyldiethoxysilane; mercaptosilanes such as 3-mercaptopropyltrimethoxysilane, 3-mercaptopropyltriethoxysilane, and 3-mercaptopropylmethyldimethoxysilane; vinylsilanes such as vinyltriethoxysilane, vinyltrimethoxysilane, and vinyltrichlorosilane; isocyanate silanes such as 3-isocyanatepropyltriethoxysilane; ureidosilanes such as 3-ureidopropyltrimethoxysilane and 3-ureidopropyltriethoxysilane; (5-norbornene-2-yl)alkylsilanes such as (5-norbornene-2-yl)trimethoxysilane, (5-norbornene-2-yl)triethoxysilane, and (5-norbornene-2-yl)ethyltrimethoxysilane; and phenylsilanes such as phenyltrimethoxysilane.

A silicone resin powder may be added to the curable resin composition. The silicone resin powder is a cured product powder having a structure in which siloxane bonds are crosslinked in a three-dimensional network manner represented by $(RSiO_{3/2})_n$. The powder suitably has an average particle diameter of 0.1 to 10 µm. Specific examples thereof include KMP-590 (manufactured by Shin-Etsu Silicone), KMP-701 (manufactured by Shin-Etsu Silicone), X-52-854 (manufactured by Shin-Etsu Silicone), X-52-1621 (manufactured by Shin-Etsu Silicone), XC99-B5664 (manufactured by Momentive Performance Materials Inc.), XC99-A8808 (manufactured by Momentive Performance Materials Inc.), and Tospearl 120 (manufactured by Momentive Performance Materials Inc.). The powders can be used alone or suitably in mixtures of two or more.

The curable resin composition according to the present invention can be obtained by mixing the above cyanate ester compound (A), and the cyanate ester compound (B) represented by the above general formula (II) or (III), the epoxy resin (C), the maleimide compound (D), and the benzoxazine compound and/or the compound having a polymerizable unsaturated group or various additives, if needed, with a solvent using known mixers such as a high-speed mixer, a nauta mixer, a ribbon-type blender, a kneader, an intensive mixer, a universal mixer, a dissolver, and a static mixer. A method for adding the cyanate ester compound, the various additives, and the solvent in the case of mixing is not particularly limited.

A cured product can be obtained by curing the curable resin composition according to the present invention by heat and light or the like. The cured product can be obtained by melting the curable resin composition or dissolving the curable resin composition in a solvent, thereafter filling the curable resin composition into a mold, and curing the curable resin composition under an ordinary condition. When a curing temperature is too low in the case of heat curing, the curing does not proceed. When the curing temperature is too high, the cured product is deteriorated. Therefore, the curing temperature is preferably in the range of 120° C. to 300° C.

<Application of Curable Resin Composition>

A sealing material can be produced using the above curable resin composition. A method for producing the sealing material is not particularly limited. The sealing material can be obtained by mixing the above components using a known mixer. A method for adding the cyanate ester compound, the various additives, and the solvent in the case of mixing is not particularly limited.

An inorganic and/or an organic fiber base material prepreg can be produced using the curable resin composition according to the present invention. A method for producing the prepreg is not particularly limited. Known methods used for a printed wiring material can be applied. For example, a method for impregnating an inorganic and/or an organic fiber base material with a resin composition varnish, drying the inorganic and/or the organic fiber base material, and putting the inorganic and/or the organic fiber base material into a B stage to form a prepreg, or the like can be applied.

The curable resin composition according to the present invention can be used to produce a metal-clad laminate and a multilayer plate. Methods for producing the laminates are not particularly limited. The laminate can be obtained by subjecting the above prepreg and a metal foil to heat pressure molding with the prepreg and the metal foil laminated. Although a heating temperature is not particularly limited, the heating temperature is preferably 65 to 300° C., and particularly preferably 120 to 270° C. Although a pressurizing pressure is not particularly limited, the pressurizing pressure is preferably 2 to 5 MPa, and more preferably 2.5 to 4 MPa.

A fiber-reinforced composite material can be produced using the curable resin composition according to the present invention. The form and arrangement of a reinforced fiber are not particularly limited, and can be suitably selected from a textile, a nonwoven fabric, a mat, a knit, a braid, a unidirectional strand, a roving, and a chopped strand. A preform (one obtained by laminating woven base fabrics containing reinforced fibers, one obtained by integrally stitching the woven base fabrics by stitch threads, or a fiber structure such as three-dimensional textile or a braid) can also be applied as the form of the reinforced fiber. Specific examples of a method for producing the fiber-reinforced composite material include liquid composite molding methods, resin film infusion methods, filament winding methods, hand lay-up methods, and pultrusion methods. Among these, in a resin transfer molding method which is one of the liquid composite molding methods, a material other than the preform such as a metal plate, a foam core, and a honeycomb core can previously set in a forming die and the resin transfer molding method can apply to various applications, thereby being preferably used when a composite material having a comparatively complicated shape is mass-produced in a short time.

Because the curable resin composition according to the present invention has excellent low thermal expansibility and high heat resistance, the curable resin composition is extremely useful as a highly-functional polymer material. The curable resin composition is preferably used for electrical insulating materials, sealing materials, adhesives, lamination materials, resists, and build-up laminate sheet materials as materials having excellent thermal, electrical, and mechanical properties. Additionally, the curable resin composition is preferably used for fixing materials, structural members, reinforcing materials, and embossing materials or the like in the fields of civil engineering and construction, electric and electronics, automobiles, railways, shipping, aircraft, sporting goods, arts and crafts or the like. Among these, the curable resin composition is suitable for semiconductor sealing materials, adhesives for electronic parts, aircraft structural members, satellite structural members, and railway vehicle structural members which require low thermal expansibility, flame resistance, and high mechanical strength.

EXAMPLES

Hereinafter, the present invention is described further specifically with reference to the following examples, however, the present invention should not be limited thereto.

Synthesis of Cyanate Ester Compound

Synthesis Example 1

Synthesis of 1,1-bis(4-cyanatophenyl)isobutane (Abbreviated as Bis-IB CN)

24.2 g (100 mmol) of 1,1-bis(4-hydroxyphenyl)isobutane (manufactured by Wako Pure Chemical Industries, Ltd.) and 28.3 g (280 mmol) of triethyl amine were dissolved in 100 mL of tetrahydrofuran (solution 1). At −10° C., the solution 1 was dropwise added to a mixed solution of a methylene chloride solution (46.2 g) of cyanogen chloride (18.4 g (300 mmol)) and tetrahydrofuran (100 mL), taking 1.5 hours. After the completion of the reaction was confirmed, the reaction liquid was condensed. The obtained crude product was dissolved in 300 mL of methylene chloride. The obtained liquid was washed with 1 M hydrochloric acid and distilled water, and was then dried over anhydrous magnesium sulfate. The methylene chloride was distilled away to obtain 28.3 g of desired 1,1-bis(4-cyanatophenyl)isobutane. The structure of the compound obtained as described above was identified by an NMR spectrum. The NMR spectrum is shown in FIG. 1.

1H-NMR: (270 MHz, chloroform-d, internal standard TMS) δ (ppm) 0.88 (d, 6H), 2.41 (m, 1H), 3.51 (d, 1H), 7.20-7.35 (complex, 8H)

Synthesis Example 2

Synthesis of 1,1-bis(4-cyanatophenyl)ethane (Abbreviated as Bis-E CN)

Figure 2:
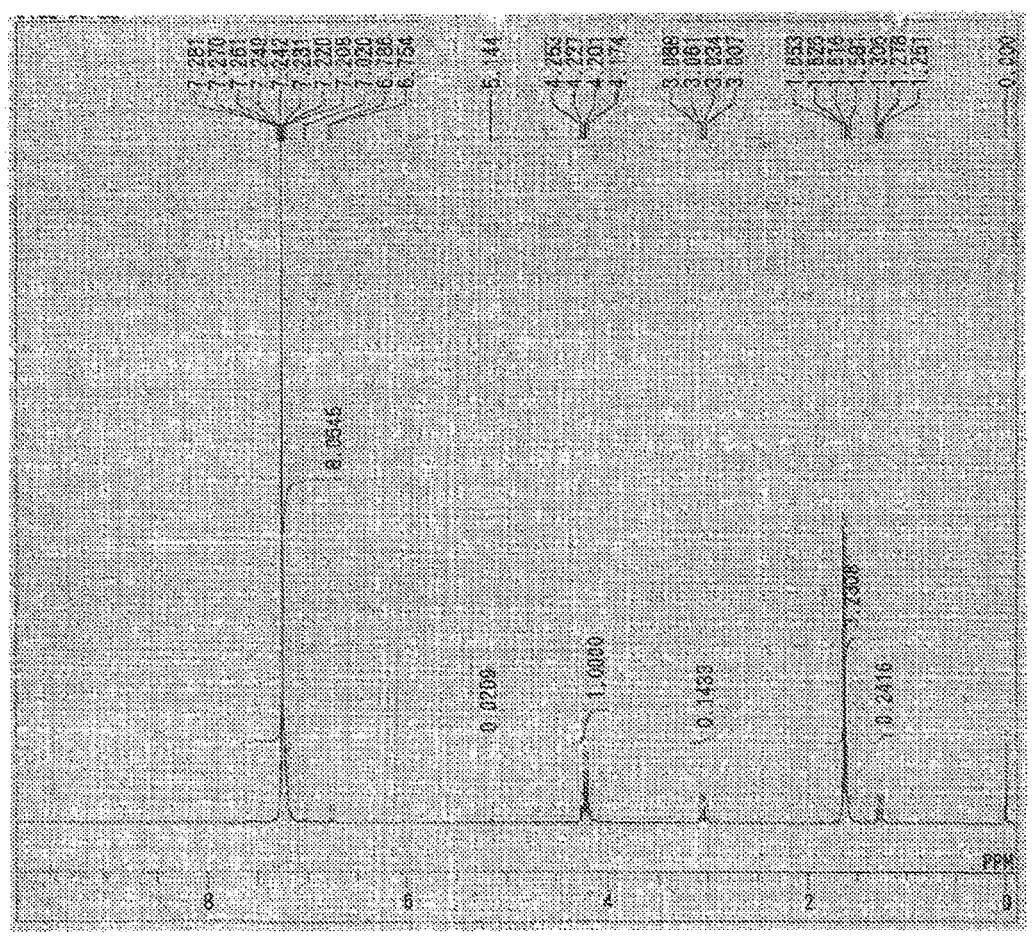
FIG. 2 shows a ¹H-NMR chart of 1,1-bis(4-cyanatophenyl)ethane obtained in Synthesis Example 2.

23.1 g of 1,1-bis(4-cyanatophenyl)ethane was obtained in the same manner as in Synthesis Example 1 except that 1,1-bis(4-hydroxyphenyl)ethane (manufactured by Wako Pure Chemical Industries, Ltd.) was used in place of 1,1-bis(4-hydroxyphenyl)isobutane. The structure of the compound obtained as described above was identified by an NMR spectrum. The NMR spectrum is shown in FIG. 2.

1H-NMR: (270 MHz, chloroform-d, internal standard TMS) δ (ppm) 1.62 (d, 3H), 4.22 (q, 1H), 7.42 (complex, 8H)

Synthesis Example 3

Synthesis of bis(4-cyanatophenyl)ether (Abbreviated as Bis-Ether CN)

Figure 3:
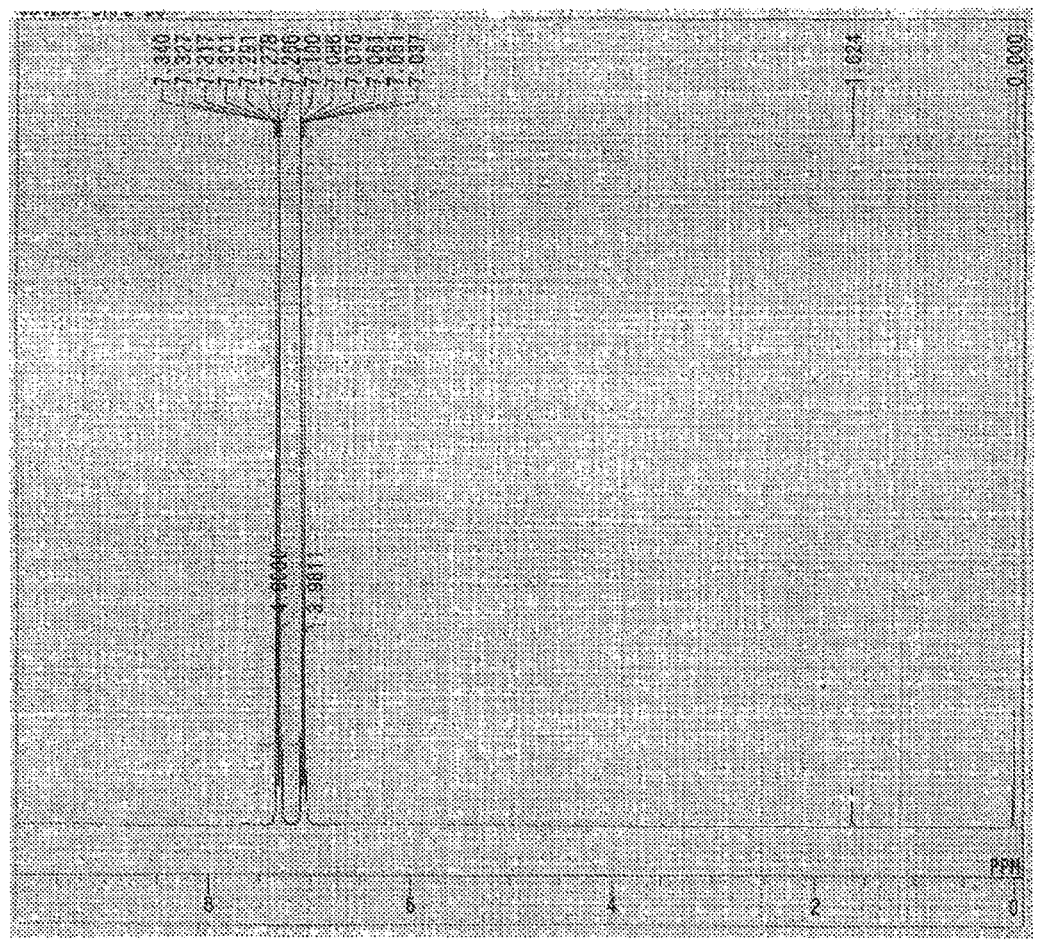
FIG. 3 shows a ¹H-NMR chart of bis(4-cyanatophenyl) ether obtained in Synthesis Example 3.

22.0 g of bis(4-cyanatophenyl)ether was obtained in the same manner as in the Synthesis Example 1 except that bis(4-hydroxyphenyl)ether (manufactured by Tokyo Kasei Kogyo Co., Ltd.) was used in place of 1,1-bis(4-hydroxyphenyl)isobutane. The structure of the compound obtained as described above was identified by an NMR spectrum. The NMR spectrum is shown in FIG. 3.

1H-NMR: (270 MHz, chloroform-d, internal standard TMS) δ (ppm) 7.07 (d, 4H), 7.31 (d, 4H)

Synthesis Example 4

Synthesis of 1,1-bis(4-cyanatophenyl)cyclohexane (Abbreviated as Bis-Z CN)

Figure 4:
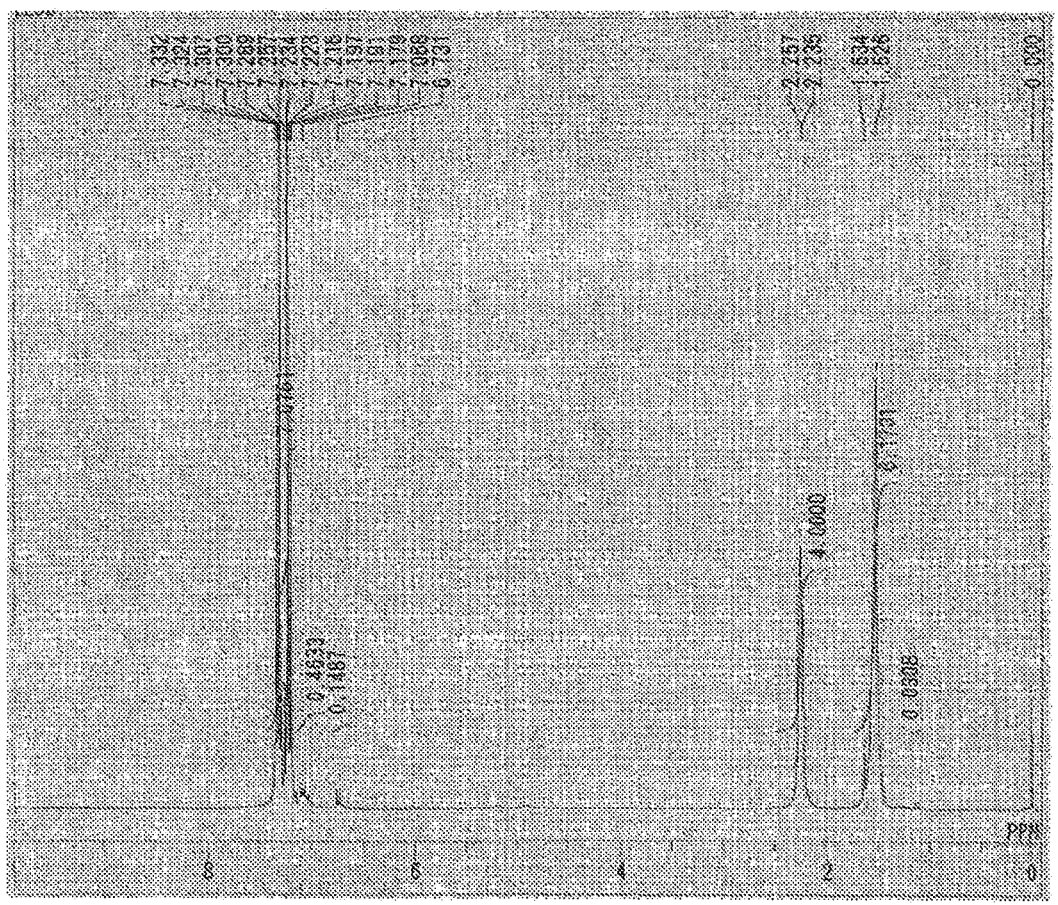
FIG. 4 shows a ¹H-NMR chart of 1,1-bis(4-cyanatophenyl)cyclohexane obtained in Synthesis Example 4.

27.3 g of 1,1-bis(4-cyanatophenyl)cyclohexane was obtained in the same manner as in Synthesis Example 1 except that 1,1-bis(4-hydroxyphenyl)cyclohexane (manufactured by Wako Pure Chemical Industries, Ltd.) was used in place of 1,1-bis(4-hydroxyphenyl)isobutane. The structure of the compound obtained as described above was identified by an NMR spectrum. The NMR spectrum is shown in FIG. 4.

1H-NMR: (270 MHz, chloroform-d, internal standard TMS) δ (ppm) 1.53 (m, 6H), 2.24 (m, 4H), 7.16-7.33 (complex, 8H)

Synthesis Example 5

Synthesis of 2,2-bis(4-cyanatophenyl)butane (Abbreviated as Bis-MEK CN)

Figure 5:
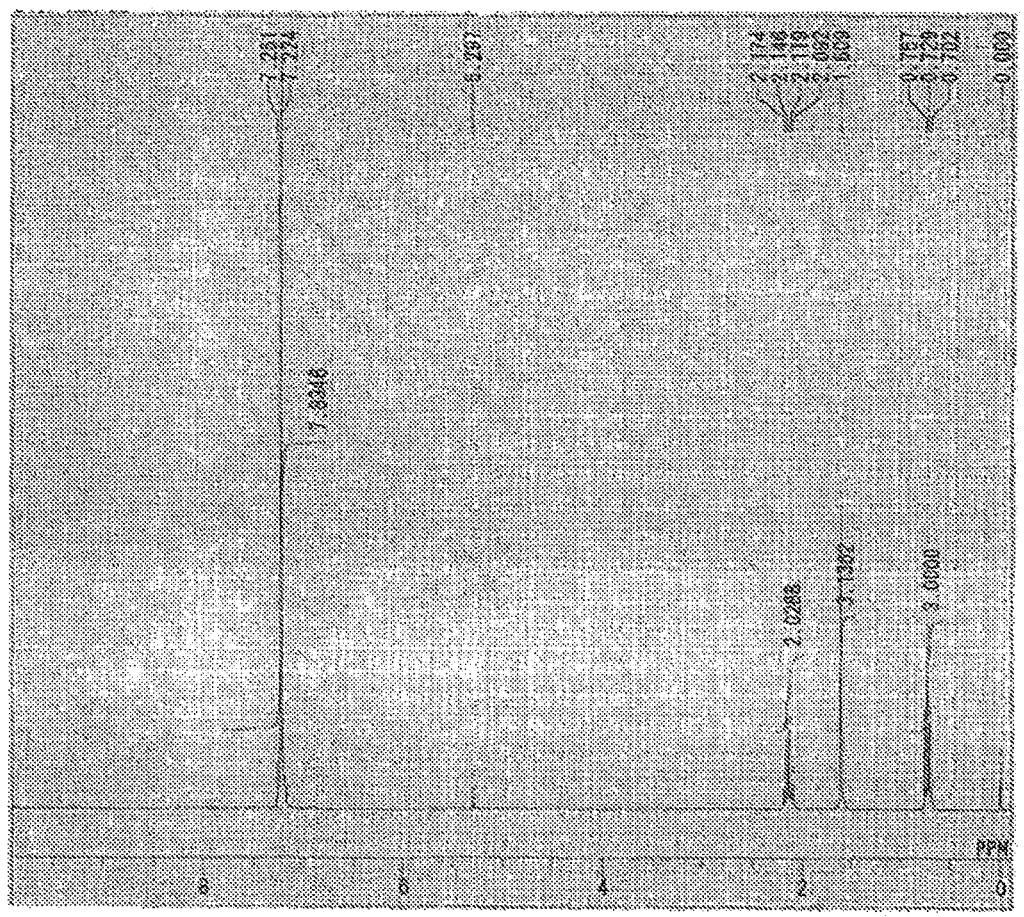
FIG. 5 shows a ¹H-NMR chart of 2,2-bis(4-cyanatophenyl)butane obtained in Synthesis Example 5.

25.1 g of 2,2-bis(4-cyanatophenyl)butane was obtained in the same manner as in Synthesis Example 1 except that 2,2-bis(4-hydroxyphenyl)butane (manufactured by Tokyo Kasei Kogyo Co., Ltd.) was used in place of 1,1-bis(4-hydroxyphenyl)isobutane. The structure of the compound obtained as described above was identified by an NMR spectrum. The NMR spectrum is shown in FIG. 5.

1H-NMR: (270 MHz, chloroform-d, internal standard TMS) δ (ppm) 0.73 (t, 3H), 1.61 (s, 3H), 2.13 (q, 2H), 7.22 (complex, 8H)

Synthesis Example 6

Synthesis of tris(4-cyanatophenyl)-1,1,1-methane (Abbreviated as TRPCN)

Tris(4-cyanatophenyl)-1,1,1-methane was obtained from tris(4-hydroxyphenyl)-1,1,1-methane based on a method described in the synthesis example of Japanese Patent Laid-Open No. 2006-290933.

Synthesis Example 7

Synthesis Of Naphthol Aralkyl-Based Cyanate Ester (Abbreviated as SNCN)

A naphthol aralkyl-based cyanate ester was obtained from an α-naphthol aralkyl resin based on a method described in Synthesis Example 1 of Japanese Patent Laid-Open No. 2006-193607.

Preparation of Curable Resin Composition

Example 1

100 parts by mass of Bis-IB CN obtained in the synthesis example 1 and zinc octylate (manufactured by NIHON KAGAKU SANGYO CO., Ltd., Nikka Octhix Zinc (trademark), metal content: 18%) were heated and degassed with a vacuum pump to obtain a composition. The presence of an insoluble portion at 50° C. and the curing progress for the obtained composition were visually confirmed.
<Production of Cured Product>

The composition obtained as described above was reheated. The composition was cast into a mold formed of a glass plate (120 mm×120 mm×5 mm), a polyimide film ("Kapton 200H" manufactured by Toray DuPont), and a fluoro rubber-made O ring ("S-100" manufactured by Morisei Kako Co., Ltd.), and was cured by heating in an oven at 250° C. for 4 hours. After cooling, the polyimide film was removed by polishing, thereby obtaining a cured product.

Example 2

A cured product was obtained in the same manner as in Example 1 except that 70 parts by mass of Bis-IB CN and 30 parts by mass of Bis-E CN obtained in Synthesis Example 2 were used in place of using 100 parts by mass of Bis-IB CN in Example 1.

Example 3

A cured product was obtained in the same manner as in Example 1 except that 90 parts by mass of Bis-IB CN and 10 parts by mass of Bis-Ether CN obtained in Synthesis Example 3 were used in place of using 100 parts by mass of Bis-IB CN in Example 1.

Example 4

A cured product was obtained in the same manner as in Example 1 except that 80 parts by mass of Bis-IB CN, 10 parts by mass of Bis-E CN obtained in Synthesis Example 2, and 10 parts by mass of SNCN obtained in Synthesis Example 7 were used in place of using 100 parts by mass of Bis-IB CN in Example 1.

Example 5

A cured product was obtained in the same manner as in Example 1 except that 70 parts by mass of Bis-IB CN, and 30 parts by mass of a bisphenol F-based epoxy resin (manufactured by Mitsubishi Chemical Corporation, jER 806 (trademark), abbreviated as DGEBF) were used in place of using 100 parts by mass of Bis-IB CN in Example 1, and a curing temperature in an oven was set to 200° C.

Example 6

A cured product was obtained in the same manner as in Example 1 except that 93 parts by mass of Bis-IB CN, and 7 parts by mass of a cresol novolac-based epoxy resin (manufactured by DIC Corporation, EpiclonN-680 (trademark), abbreviated as ECN) were used in place of using 100 parts by mass of Bis-IB CN in Example 1, and a curing temperature in an oven was set to 200° C.

Example 7

A cured product was obtained in the same manner as in Example 1 except that 95 parts by mass of Bis-IB CN, and 5 parts by mass of 4,4'-bismaleimide diphenylmethane (manufactured by Tokyo Kasei Kogyo Co., Ltd., abbreviated as BMI) were used in place of using 100 parts by mass of Bis-IB CN in Example 1.

Example 8

A cured product was obtained in the same manner as in Example 1 except that 85 parts by mass of Bis-IB CN, 5 parts by mass of DGEBF, 5 parts by mass of a bisphenol A-based epoxy resin (manufactured by Mitsubishi Chemical Corporation, jER 828 (trademark), abbreviated as DGEBA), and 5 parts by mass of a maleimide compound (manufactured by KI CHEMICAL INDUSTRY CO., LTD., BMI-70 (trademark)) were used in place of using 100 parts by mass of Bis-IB CN in Example 1, and a curing temperature in an oven was set to 200° C.

Example 9

A cured product was obtained in the same manner as in Example 1 except that 100 parts by mass of Bis-E CN obtained in Synthesis Example 2 was used in place of using 100 parts by mass of Bis-IB CN in Example 1.

Example 10

A cured product was obtained in the same manner as in Example 1 except that 100 parts by mass of 2,2-bis(4-cyanatophenyl)propane (manufactured by MITSUBISHI GAS CHEMICAL COMPANY, INC., abbreviated as Bis-A CN) was used in place of using 100 parts by mass of Bis-IB CN in Example 1.

Example 11

A cured product was obtained in the same manner as in Example 1 except that 100 parts by mass of Bis-Ether CN obtained in the Synthesis Example 3 was used in place of using 100 parts by mass of Bis-IB CN in Example 1.

Example 12

A cured product was obtained in the same manner as in Example 1 except that 100 parts by mass of Bis-Z CN obtained in Synthesis Example 4 was used in place of using 100 parts by mass of Bis-IB CN in Example 1.

Example 13

A cured product was obtained in the same manner as in Example 1 except that 100 parts by mass of Bis-MEK CN obtained in Synthesis Example 5 was used in place of using 100 parts by mass of Bis-IB CN in Example 1.

Example 14

A cured product was obtained in the same manner as in Example 1 except that 100 parts by mass of TRPCN obtained in Synthesis Example 6 was used in place of using 100 parts by mass of Bis-IB CN in Example 1.

Example 15

A cured product was obtained in the same manner as in Example 1 except that 50 parts by mass of Bis-E CN obtained in Synthesis Example 2 and 50 parts by mass of DGEBF were used in place of using 100 parts by mass of Bis-IB CN in Example 1, and a curing temperature in an oven was set to 200° C.

Example 16

A cured product was obtained in the same manner as in Example 1 except that 30 parts by mass of Bis-A CN and 70 parts by mass of DGEBF were used in place of using 100 parts by mass of Bis-IB CN in Example 1, and a curing temperature in an oven was set to 200° C.

Example 17

A cured product was obtained in the same manner as in Example 1 except that 100 parts by mass of DGEBF was used in place of using 100 parts by mass of Bis-IB CN in Example 1; 2 parts by mass of 2-ethyl-4-methylimidazole (manufactured by Wako Pure Chemical Industries, Ltd., abbreviated as 2E4MZ) was used in place of using 0.02 parts by mass of zinc octylate; and a curing temperature in an oven was set to 200° C.

Example 18

A cured product was obtained in the same manner as in Example 1 except that 95 parts by mass of Bis-E CN obtained in Synthesis Example 2 and 5 parts by mass of BMI were used in place of using 100 parts by mass of Bis-IB CN in Example 1.

Example 19

A cured product was obtained in the same manner as in Example 1 except that 70 parts by mass of Bis-A CN and 30 parts by mass of DGEBF were used in place of using 100 parts by mass of Bis-IB CN in Example 1.

<Evaluation of Cured Products>

The glass transition temperature and coefficient of linear expansion of each of the cured products obtained as described above were measured. The glass transition temperature was measured based on JIS-K7244-7-2007. Dynamic viscoelasticity measurement was conducted using a dynamic viscoelasticity measuring device (AR2000 manufactured by TA Instruments) under measurement conditions of a start temperature of 100° C., an end temperature of 350° C., a temperature increase rate of 3° C./min, and a measurement frequency of 1 Hz. The maximum value of loss tangent (tan δ) obtained at that time was defined as the glass transition temperature. A coefficient of linear expansion was measured based on JIS-K-7197-1991. A test piece (5 mm×5 mm×5 mm) was set in a thermomechanical analyzer (TMA/SS7100 manufactured by SII NanoTechnology Inc.). Thermomechanical analysis was conducted in an expansion/compression mode under measurement conditions of a start temperature of 100° C., an end temperature of 300° C., a temperature increase rate of 5° C./min, and a load of 0.05 N, to measure an average thermal expansion amount per 1° C. at a predetermined temperature. Average coefficients of linear expansion at 200° C. to 300° C. were measured in examples other than Examples 5, 6, 8, 14, 15, and 16. Average coefficients of linear expansion at 150° C. to 250° C. were measured in Examples 5, 6, 8, 14, 15, 16, and 19. The measurement results are shown in the following Table 1. The units of numerical values in Table 1 are represented by part by mass. Portions described as "-" in Table 1 mean that the relevant materials are not blended. In the glass transition temperature (Tg) in Table 1, "350 or more" means that the maximum peak value of tan δ was not clear within a measurement temperature range and Tg could not be confirmed within the range.

TABLE 1

| resin composition | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| cyanate ester | Bis-IB CN | 100 | 70 | 90 | 80 | 70 | 93 | 95 | 85 | — | — |
| | Bis-E CN | — | 30 | — | 10 | — | — | — | — | 100 | — |
| | Bis-Ether CN | — | — | 10 | — | — | — | — | — | — | — |
| | SNCN | — | — | — | 10 | — | — | — | — | — | — |
| | DGEBF | — | — | — | — | 30 | — | — | 5 | — | — |
| | DGEBA | — | — | — | — | — | — | — | 5 | — | — |
| | ECN | — | — | — | — | — | 7 | — | — | — | — |
| | BMI | — | — | — | — | — | — | — | 5 | — | — |
| | BMI-70 | — | — | — | — | — | — | — | 5 | — | — |
| | Bis-A CN | — | — | — | — | — | — | — | — | — | 100 |
| | Bis-Z CN | — | — | — | — | — | — | — | — | — | — |
| | Bis-MEK CN | — | — | — | — | — | — | — | — | — | — |
| | TRPCN | — | — | — | — | — | — | — | — | — | — |
| polymerization catalyst | zinc octylate | 0.02 | 0.02 | 0.02 | 0.02 | 0.02 | 0.02 | 0.02 | 0.02 | 0.02 | 0.02 |
| | 2E4MZ | — | — | — | — | — | — | — | — | — | — |
| evaluation results | properties | transparent solution | transparent solution | transparent solution | transparent solution | transparent solution | transparent solution | transparent solution | transparent solution | transparent solution | white solid |
| | Tg (° C.) | 350 or more | 304 | 295 | 289 | 217 | 301 | 274 | 274 | 274 | 300 |
| | coefficient of linear expansion (ppm/° C.) | 77 | 74 | 79 | 112 | 132 | 84 | 73 | 96 | 122 | 96 |

| resin composition | | Example 11 | Example 12 | Example 13 | Example 14 | Example 15 | Example 16 | Example 17 | Example 18 | Example 19 |
|---|---|---|---|---|---|---|---|---|---|---|
| cyanate ester | Bis-IB CN | — | — | — | — | — | — | — | — | — |
| | Bis-E CN | — | — | — | — | 50 | — | — | 95 | — |
| | Bis-Ether CN | 100 | — | — | — | — | — | — | — | — |
| | SNCN | — | — | — | — | — | — | — | — | — |
| | DGEBF | — | — | — | — | 50 | 70 | 100 | — | 30 |
| | DGEBA | — | — | — | — | — | — | — | — | — |
| | ECN | — | — | — | — | — | — | — | — | — |
| | BMI | — | — | — | — | — | — | — | 5 | — |
| | BMI-70 | — | — | — | — | — | — | — | — | — |
| | Bis-A CN | — | — | — | — | — | 30 | — | — | 70 |
| | Bis-Z CN | — | 100 | — | — | — | — | — | — | — |
| | Bis-MEK CN | — | — | 100 | — | — | — | — | — | — |
| | TRPCN | — | — | — | 100 | — | — | — | — | — |
| polymerization catalyst | zinc octylate | 0.02 | 0.02 | 0.02 | 0.02 | 0.02 | 0.02 | — | 0.02 | 0.02 |
| | 2E4MZ | — | — | — | — | — | — | 2.00 | — | — |

TABLE 1-continued

| evaluation results | properties | white solid | brown solid | transparent solution | white solid | transparent solution | transparent solution | transparent solution | transparent solution | transparent solution |
|---|---|---|---|---|---|---|---|---|---|---|
| | Tg (° C.) | 298 | 304 | 298 | 350 or more | 178 | 157 | 124 | 229 | 206 |
| | coefficient of linear expansion (ppm/° C.) | 95 | 91 | 128 | 51 | 170 | 201 | 187 | 115 | 141 |

The invention claimed is:

1. A cyanate ester compound (A) represented by the following formula (I):

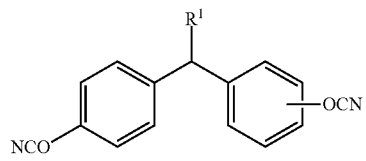

wherein the cyanate ester compound is 1,1-bis(4-cyanatophenyl)isobutane.

2. A curable resin composition comprising a cyanate ester compound (A) according to claim 1.

3. The curable resin composition according to claim 2, wherein the curable resin composition is a non-crystalline liquid at 50° C.

4. The curable resin composition according to claim 2, further comprising one or more selected from the group consisting of a cyanate ester compound (B) represented by the following general formula (II):

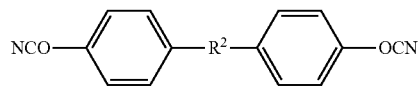

wherein $R^2$ represents any one selected from the group consisting of the following general formulae (i) to (v):

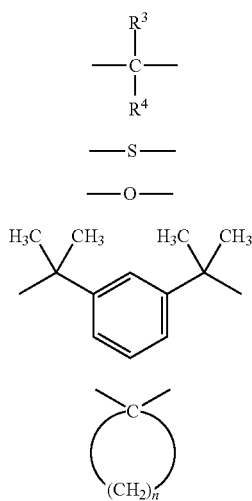

wherein each of $R^3$ and $R^4$ represents a hydrogen atom, or an alkyl group having 1 to 8 carbon atoms or a trifluoromethyl group, and n represents an integer of 4 to 7;

or the following general formula (III):

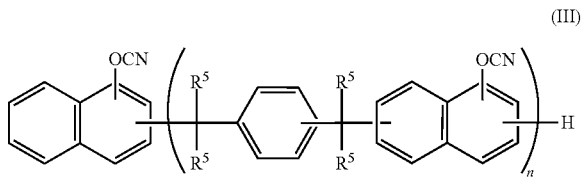

wherein $R^5$ represents hydrogen or a methyl group; n represents an integer of 1 to 50; and the cyanate ester compound (B) represented by the general formula (III) may be a mixture of compounds having different n, an epoxy resin (C), and a maleimide compound (D).

5. The curable resin composition according to claim 4, wherein the epoxy resin is one or more selected from the group consisting of a bisphenol A-based epoxy resin, a bisphenol F-based epoxy resin, a phenol novolac-based epoxy resin, and a dihydroxy naphthalene-based epoxy resin.

6. The curable resin composition according to claim 4, wherein the maleimide compound is a compound represented by the following general formula (IV):

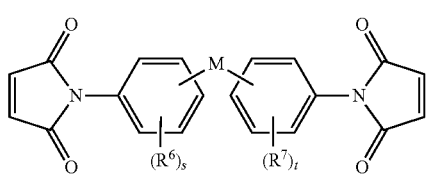

wherein each of $R^5$ and $R^6$ independently represents a hydrogen atom, a halogen atom, or an alkyl group having 1 to 3 carbon atoms; each of e and f represents an integer of 1 to 4; and M represents a single bond, an alkylene group having 1 to 5 carbon atoms, an alkylidene group having 1 to 5 carbon atoms, or an arylene group having 6 to 14 carbon atoms.

7. A curable resin composition comprising a cyanate ester compound (A) selected from the group consisting of
1,1-bis(4-cyanatophenyl)isobutane,
1,1-bis(4-cyanatophenyl)-3-methylbutane,
1,1-bis(4-cyanatophenyl)-2-methylbutane,
1,1-bis(4-cyanatophenyl)-2,2-dimethylpropane,
1,1-bis(4-cyanatophenyl)-4-methylpentane,
1,1-bis(4-cyanatophenyl)-3-methylpentane,
1,1-bis(4-cyanatophenyl)-2-methylpentane, 1,1-bis(4-cyanatophenyl)-2,3-dimethylbutane,
1,1-bis(4-cyanatophenyl)-3,3-dimethylbutane,
bis(4-cyanatophenyl)cyclopentylmethane,
bis(4-cyanatophenyl)cyclohexyl methane,
bis(4-cyanatophenyl)phenylmethane,
1,1-bis(4-cyanatophenyl)-2-methylhexane,
1,1-bis(4-cyanatophenyl)-3-methylhexane,
1,1-bis(4-cyanatophenyl)-4-methylhexane,
1,1-bis(4-cyanatophenyl)-5-methylhexane,
1,1-bis(4-cyanatophenyl)-3,4-dimethylpentane,
1,1-bis(4-cyanatophenyl)-2,3-dimethylpentane,
1,1-bis(4-cyanatophenyl)-3-ethylpentane,
1,1-bis(4-cyanatophenyl)-2-ethylpentane,
bis(4-cyanatophenyl)-1-naphthylmethane,
1,1-bis(4-cyanatophenyl)-2-phenylmethylhexane,
1-(2-cyanatophenyl)-1-(4-cyanatophenyl)propane,
1-(2-cyanatophenyl)-1-(4-cyanatophenyl)butane,
1-(2-cyanatophenyl)-1-(4-cyanatophenyl)isobutane,
1-(2-cyanatophenyl)-1-(4-cyanatophenyl)pentane,
1-(2-cyanatophenyl)-1-(4-cyanatophenyl)-3-methylbutane,
1-(2-cyanatophenyl)-1-(4-cyanatophenyl)-2-methylbutane,
1-(2-cyanatophenyl)-1-(4-cyanatophenyl)-2,2-dimethylpropane,
1-(2-cyanatophenyl)-1-(4-cyanatophenyl)hexane,
1-(2-cyanatophenyl)-1-(4-cyanatophenyl)-4-methylpentane,
1-(2-cyanatophenyl)-1-(4-cyanatophenyl)-3-methylpentane,
1-(2-cyanatophenyl)-1-(4-cyanatophenyl)-2-methylpentane,
1-(2-cyanatophenyl)-1-(4-cyanatophenyl)-2,3-dimethylbutane,
1-(2-cyanatophenyl)-1-(4-cyanatophenyl)-3,3-dimethylbutane,
[(2-cyanatophenyl)-(4-cyanatophenyl)methyl]cyclopentane,
[(2-cyanatophenyl)-(4-cyanatophenyl)methyl]cyclohexane,
2,4'-dicyanatotriphenylmethane,
1-(2-cyanatophenyl)-1-(4-cyanatophenyl)heptane,
1-(2-cyanatophenyl)-1-(4-cyanatophenyl)-2-methylhexane,
1-(2-cyanatophenyl)-1-(4-cyanatophenyl)-3-methylhexane,
1-(2-cyanatophenyl)-1-(4-cyanatophenyl)-4-methylhexane,
1-(2-cyanatophenyl)-1-(4-cyanatophenyl)-5-methylhexane,
1-(2-cyanatophenyl)-1-(4-cyanatophenyl)-3,4-dimethylpentane,
1-(2-cyanatophenyl)-1-(4-cyanatophenyl)-2,3-dimethylpentane,
1-(2-cyanatophenyl)-1-(4-cyanatophenyl)-3-ethylpentane,
1-(2-cyanatophenyl)-1-(4-cyanatophenyl)-2-ethylpentane, and
[(2-cyanatophenyl)-(4-cyanatophenyl)methyl]naphthalene, and
further comprising one or more selected from the group consisting of a cyanate ester compound (B) represented by the following general formula (II):

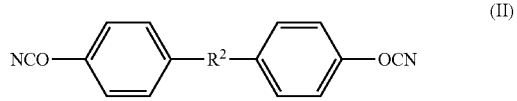

wherein $R^2$ represents any one selected from the group consisting of the following general formulae (i) to (v):

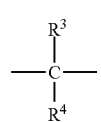 (i)

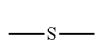 (ii)

 (iii)

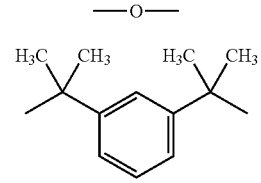 (iv)

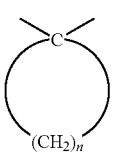 (v)

wherein each of $R^1$ and $R^4$ represents a hydrogen atom, or an alkyl group having 1 to 8 carbon atoms or a trifluoromethyl group, and n represents an integer of 4 to 7;

or the following general formula (III):

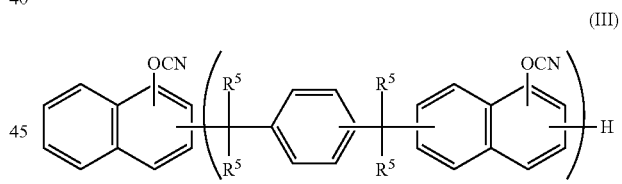

wherein $R^5$ represents hydrogen or a methyl group; n represents an integer of 1 to 50; and the cyanate ester compound (B) represented by the general formula (III) may be a mixture of compounds having different n, an epoxy resin (C), and a maleimide compound (D); and
wherein the curable resin composition comprises 0 to 250 parts by mass of the cyanate ester compound (B), 0 to 250 parts by mass of the epoxy resin (C), and 0 to 100 parts by mass of the maleimide compound (D), based on 100 parts by mass of the cyanate ester compound (A).

8. The curable resin composition according to claim 7, wherein the curable resin composition comprises 0 to 100 parts by mass of the cyanate ester compound (B), 0 to 100 parts by mass of the epoxy resin (C), and 0 to 50 parts by mass of the maleimide compound (D), based on 100 parts by mass of the cyanate ester compound (A).

9. A curable resin composition comprising a cyanate ester compound (A) selected from the group consisting of 1,1-bis(4-cyanatophenyl)isobutane,
1,1-bis(4-cyanatophenyl)-3-methylbutane,
1,1-bis(4-cyanatophenyl)-2-methylbutane,
1,1-bis(4-cyanatophenyl)-2,2-dimethylpropane,
1,1-bis(4-cyanatophenyl)-4-methylpentane,
1,1-bis(4-cyanatophenyl)-3-methylpentane,
1,1-bis(4-cyanatophenyl)-2-methylpentane,
1,1-bis(4-cyanatophenyl)-2,3-dimethylbutane,
1,1-bis(4-cyanatophenyl)-3,3-dimethylbutane,
bis(4-cyanatophenyl)cyclopentylmethane,
bis(4-cyanatophenyl)cyclohexyl methane,
bis(4-cyanatophenyl)phenylmethane,
1,1-bis(4-cyanatophenyl)-2-methylhexane,
1,1-bis(4-cyanatophenyl)-3-methylhexane,
1,1-bis(4-cyanatophenyl)-4-methylhexane,
1,1-bis(4-cyanatophenyl)-5-methylhexane,
1,1-bis(4-cyanatophenyl)-3,4-dimethylpentane,
1,1-bis(4-cyanatophenyl)-2,3-dimethylpentane,
1,1-bis(4-cyanatophenyl)-3-ethylpentane,
1,1-bis(4-cyanatophenyl)-2-ethylpentane,
bis(4-cyanatophenyl)-1-naphthylmethane,
1,1-bis(4-cyanatophenyl)-2-phenylmethylhexane,
1-(2-cyanatophenyl)-1-(4-cyanatophenyl)propane,
1-(2-cyanatophenyl)-1-(4-cyanatophenyl)butane,
1-(2-cyanatophenyl)-1-(4-cyanatophenyl)isobutane,
1-(2-cyanatophenyl)-1-(4-cyanatophenyl)pentane,
1-(2-cyanatophenyl)-1-(4-cyanatophenyl)-3-methylbutane,
1-(2-cyanatophenyl)-1-(4-cyanatophenyl)-2-methylbutane,
1-(2-cyanatophenyl)-1-(4-cyanatophenyl)-2,2-dimethylpropane,
1-(2-cyanatophenyl)-1-(4-cyanatophenyl)hexane,
1-(2-cyanatophenyl)-1-(4-cyanatophenyl)-4-methylpentane,
1-(2-cyanatophenyl)-1-(4-cyanatophenyl)-3-methylpentane,
1-(2-cyanatophenyl)-1-(4-cyanatophenyl)-2-methylpentane,
1-(2-cyanatophenyl)-1-(4-cyanatophenyl)-2,3-dimethylbutane,
1-(2-cyanatophenyl)-1-(4-cyanatophenyl)-3,3-dimethylbutane,
[(2-cyanatophenyl)-(4-cyanatophenyl)methyl]cyclopentane,
[(2-cyanatophenyl)-(4-cyanatophenyl)methyl]cyclohexane,
2,4'-dicyanatotriphenylmethane,
1-(2-cyanatophenyl)-1-(4-cyanatophenyl)heptane,
1-(2-cyanatophenyl)-1-(4-cyanatophenyl)-2-methylhexane,
1-(2-cyanatophenyl)-1-(4-cyanatophenyl)-3-methylhexane,
1-(2-cyanatophenyl)-1-(4-cyanatophenyl)-4-methylhexane,
1-(2-cyanatophenyl)-1-(4-cyanatophenyl)-5-methylhexane,
1-(2-cyanatophenyl)-1-(4-cyanatophenyl)-3,4-dimethylpentane,
1-(2-cyanatophenyl)-1-(4-cyanatophenyl)-2,3-dimethylpentane,
1-(2-cyanatophenyl)-1-(4-cyanatophenyl)-3-ethylpentane,
1-(2-cyanatophenyl)-1-(4-cyanatophenyl)-2-ethylpentane, and
[(2-cyanatophenyl)-(4-cyanatophenyl)methyl]naphthalene, and wherein the curable resin composition comprises a metal complex compound containing zinc as a polymerization catalyst.

10. A cured product obtained by curing the curable resin composition according to claim 9.

11. A sealing material comprising the curable resin composition according to claim 9.

12. An adhesive comprising the curable resin composition according to claim 9.

13. The curable resin composition according to claim 9, further comprising one or more selected from the group consisting of bis(4-cyanatophenyl)methane, 2,4'-dicyanatodiphenylmethane, 1,1-bis(4-cyanatophenyl)ethane, 2,2-bis(4-cyanatophenyl)propane, 2,2-bis(4-cyanatophenyl)butane, 2,2-bis(4-cyanatophenyl)4-methylpentane; 2,2-bis(4-cyanataophenyl)-1,1,1,3,3,3-hexafluropropane, 1,3-bis[2-(4-cyanatophenyl)-2-propyl]benzene, bis-(4-cyanatophenyl) ether, bis-(4-cyanatophenyl)sulfide, and 1,1-bis(4-cyanatophenyl)cyclohexane, an epoxy resin (C) and a maleimide compound (D).

14. The curable resin composition according to claim 13, wherein the epoxy resin is one or more selected from the group consisting of a bisphenol A-based epoxy resin, a bisphenol F-based epoxy resin, a phenol novolac-based epoxy resin and a dihydroxy naphthalene-based epoxy resin.

15. The curable resin composition according to claim 13, wherein the maleimide compound is a compound represented by the following general formula (IV):

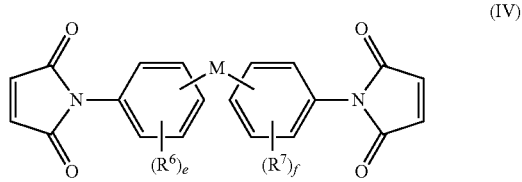

(IV)

wherein each of $R^5$ and $R^6$ independently represents a hydrogen atom, a halogen atom, or an alkyl group having 1 to 3 carbon atoms; each of e and f represents an integer of 1 to 4; and M represents a single bond, an alkylene group having 1 to 5 carbon atoms, an alkylidene group having 1 to 5 carbon atoms, or an arylene group having 6 to 14 carbon atoms.

16. A curable resin composition comprising a cyanate ester compound (A) selected from the group consisting of
1,1-bis(4-cyanatophenyl)isobutane,
1,1-bis(4-cyanatophenyl)-3-methylbutane,
1,1-bis(4-cyanatophenyl)-2-methylbutane,
1,1-bis(4-cyanatophenyl)-2,2-dimethylpropane,
1,1-bis(4-cyanatophenyl)-4-methylpentane,
1,1-bis(4-cyanatophenyl)-3-methylpentane,
1,1-bis(4-cyanatophenyl)-2-methylpentane,
1,1-bis(4-cyanatophenyl)-2,3-dimethylbutane,
1,1-bis(4-cyanatophenyl)-3,3-dimethylbutane,
bis(4-cyanatophenyl)cyclopentylmethane,
bis(4-cyanatophenyl)cyclohexyl methane,
bis(4-cyanatophenyl)phenylmethane,
1,1-bis(4-cyanatophenyl)-2-methylhexane,
1,1-bis(4-cyanatophenyl)-3-methylhexane,
1,1-bis(4-cyanatophenyl)-4-methylhexane,
1,1-bis(4-cyanatophenyl)-5-methylhexane,
1,1-bis(4-cyanatophenyl)-3,4-dimethylpentane,
1,1-bis(4-cyanatophenyl)-2,3-dimethylpentane,
1,1-bis(4-cyanatophenyl)-3-ethylpentane, 1,1-bis(4-cyanatophenyl)-2-ethylpentane,
bis(4-cyanatophenyl)-1-naphthylmethane,
1,1-bis(4-cyanatophenyl)-2-phenylmethylhexane,
1-(2-cyanatophenyl)-1-(4-cyanatophenyl)propane,
1-(2-cyanatophenyl)-1-(4-cyanatophenyl)butane,
1-(2-cyanatophenyl)-1-(4-cyanatophenyl)isobutane,
1-(2-cyanatophenyl)-1-(4-cyanatophenyl)pentane,
1-(2-cyanatophenyl)-1-(4-cyanatophenyl)-3-methylbutane,
1-(2-cyanatophenyl)-1-(4-cyanatophenyl)-2-methylbutane,
1-(2-cyanatophenyl)-1-(4-cyanatophenyl)-2,2-dimethylpropane,
1-(2-cyanatophenyl)-1-(4-cyanatophenyl)hexane,
1-(2-cyanatophenyl)-1-(4-cyanatophenyl)-4-methylpentane,
1-(2-cyanatophenyl)-1-(4-cyanatophenyl)-3-methylpentane,
1-(2-cyanatophenyl)-1-(4-cyanatophenyl)-2-methylpentane,
1-(2-cyanatophenyl)-1-(4-cyanatophenyl)-2,3-dimethylbutane,
1-(2-cyanatophenyl)-1-(4-cyanatophenyl)-3,3-dimethylbutane,
[(2-cyanatophenyl)-(4-cyanatophenyl)methyl]cyclopentane,
[(2-cyanatophenyl)-(4-cyanatophenyl)methyl]cyclohexane,
2,4'-dicyanatotriphenylmethane,
1-(2-cyanatophenyl)-1-(4-cyanatophenyl)heptane,
1-(2-cyanatophenyl)-1-(4-cyanatophenyl)-2-methylhexane,
1-(2-cyanatophenyl)-1-(4-cyanatophenyl)-3-methylhexane,
1-(2-cyanatophenyl)-1-(4-cyanatophenyl)-4-methylhexane,
1-(2-cyanatophenyl)-1-(4-cyanatophenyl)-5-methylhexane,
1-(2-cyanatophenyl)-1-(4-cyanatophenyl)-3,4-dimethylpentane,
1-(2-cyanatophenyl)-1-(4-cyanatophenyl)-2,3-dimethylpentane,
1-(2-cyanatophenyl)-1-(4-cyanatophenyl)-3-ethylpentane,
1-(2-cyanatophenyl)-1-(4-cyanatophenyl)-2-ethylpentane, and
[(2-cyanatophenyl)-(4-cyanatophenyl)methyl]naphthalene, and
further comprising one or more selected from the group consisting of
bis(4-cyanatophenyl)methane,
2,4'-dicyanatodiphenylmethane,
1,1-bis(4-cyanatophenyl)ethane,
2,2-bis(4-cyanatophenyl)propane,
2,2-bis(4-cyanatopheyl)butane,
2,2-bis(4-cyanatophenyl)4-methylpentane; 2,2-bis(4-cyanataophenyl)-1,1,1,3,3,3-hexafluropropane, 1,3-bis[2-(4-cyanatophenyl)-2-propyl]benzene,
bis-(4-cyanatophenyl)ether,
bis-(4-cyanatophenyl) sulfide, and
1,1-bis(4-cyanatophenyl)cyclohexane, an epoxy resin (C) and a maleimide compound (D),
wherein the curable resin composition comprises 0 to 250 parts by mass of the cyanate ester compound (B), 0 to 250 parts by mass of the epoxy resin (C), and 0 to 100 parts by mass of the maleimide compound (D), based on 100 parts by mass of the cyanate ester compound (A).

17. The curable resin composition according to claim 16, wherein the curable resin composition comprises 0 to 100 parts by mass of the cyanate ester compound (B), 0 to 100 parts by mass of the epoxy resin (C), and 0 to 50 parts by mass of the maleimide compound (D), based on 100 parts by mass of the cyanate ester compound (A).

* * * * *

UNITED STATES PATENT AND TRADEMARK OFFICE
CERTIFICATE OF CORRECTION

| | |
|---|---|
| PATENT NO. | : 9,453,126 B2 |
| APPLICATION NO. | : 13/878584 |
| DATED | : September 27, 2016 |
| INVENTOR(S) | : Tsubuku et al. |

It is certified that error appears in the above-identified patent and that said Letters Patent is hereby corrected as shown below:

In Claim 7 in Column 22, Line 45, please restore the "η" at the right lower side of formula (III) by changing formula (III) from:

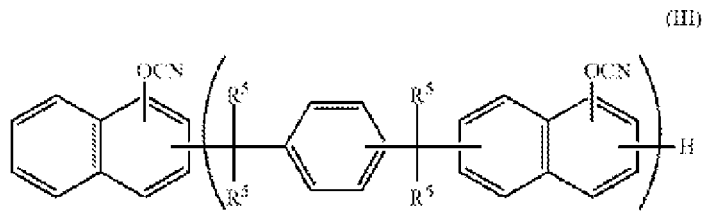

To:

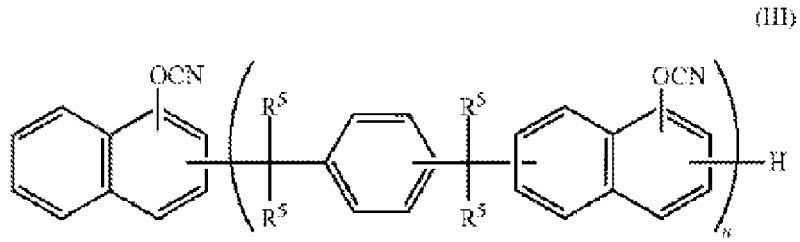

Signed and Sealed this
Fifth Day of September, 2017

Joseph Matal
*Performing the Functions and Duties of the
Under Secretary of Commerce for Intellectual Property and
Director of the United States Patent and Trademark Office*